(12) United States Patent
Bercoff et al.

(10) Patent No.: US 11,672,509 B2
(45) Date of Patent: *Jun. 13, 2023

(54) SHEAR WAVE ELASTROGRAPHY METHOD AND APPARATUS FOR IMAGING AN ANISOTROPIC MEDIUM

(71) Applicant: SUPERSONIC IMAGINE, Aix en Provence (FR)

(72) Inventors: Jeremy Bercoff, Aix en Provence (FR); Jean-Pierre Henry, Marseilles (FR)

(73) Assignee: SUPERSONIC IMAGINE, Aix-en-Provence (FR)

( * ) Notice: Subject to any disclaimer, the term of this patent is extended or adjusted under 35 U.S.C. 154(b) by 90 days.

This patent is subject to a terminal disclaimer.

(21) Appl. No.: 17/377,892

(22) Filed: Jul. 16, 2021

(65) Prior Publication Data

US 2021/0338206 A1 Nov. 4, 2021

Related U.S. Application Data

(63) Continuation of application No. 15/539,170, filed as application No. PCT/IB2014/003123 on Dec. 24, 2014, now Pat. No. 11,103,216.

(51) Int. Cl.
  *A61B 8/08* (2006.01)
  *G01S 7/52* (2006.01)
  (Continued)

(52) U.S. Cl.
  CPC ............ *A61B 8/485* (2013.01); *A61B 8/085* (2013.01); *A61B 8/463* (2013.01); *A61B 8/5207* (2013.01);
  (Continued)

(58) Field of Classification Search
  CPC ......... A61B 8/485; A61B 8/085; A61B 8/463; A61B 8/5207; G01S 7/52022; G01S 7/52042; G01S 15/8915; G01S 15/8918
  See application file for complete search history.

(56) References Cited

U.S. PATENT DOCUMENTS

| 7,252,004 B2 | 8/2007 | Fink et al. |
| 9,952,321 B2 | 4/2018 | Fink et al. |
| (Continued) | | |

FOREIGN PATENT DOCUMENTS

| CN | 101803933 A | 8/2010 |
| EP | 2 649 944 A1 | 10/2013 |
| (Continued) | | |

OTHER PUBLICATIONS

International Search Report, dated Sep. 18, 2015, from corresponding PCT application.

(Continued)

*Primary Examiner* — Bo Joseph Peng
(74) *Attorney, Agent, or Firm* — Nixon & Vanderhye

(57) ABSTRACT

A shear wave elastography method for imaging an observation field in an anisotropic medium, including an initial ultrasonic acquisition step during which initial physical parameters are acquired in at least one region of interest; a spatial characterization step during which a set of spatial characteristics of the anisotropic medium is determined on the basis of the initial physical parameter; an excitation substep during which an shear wave is generated inside the anisotropic medium on the basis of the set of spatial characteristics; and an observation substep during which the propagation of the shear wave is observed simultaneously at a multitude of points in the observation field.

28 Claims, 2 Drawing Sheets

(51) Int. Cl.
  *G01S 15/89* (2006.01)
  *A61B 8/00* (2006.01)

(52) U.S. Cl.
  CPC ...... *G01S 7/52022* (2013.01); *G01S 7/52042* (2013.01); *G01S 15/8915* (2013.01); *G01S 15/8918* (2013.01)

(56) References Cited

U.S. PATENT DOCUMENTS

| | | |
|---|---|---|
| 2002/0016557 A1 | 2/2002 | Duarte et al. |
| 2004/0068184 A1 | 4/2004 | Trahey et al. |
| 2009/0163805 A1* | 6/2009 | Sunagawa ............ G01S 7/52042 600/438 |
| 2010/0240994 A1* | 9/2010 | Zheng ..................... A61B 8/00 600/440 |
| 2010/0312116 A1 | 12/2010 | Pernot et al. |
| 2011/0028838 A1 | 2/2011 | Pernot et al. |
| 2013/0144165 A1* | 6/2013 | Ebbini ................. A61B 8/0891 600/439 |
| 2013/0289402 A1 | 10/2013 | Tabaru et al. |
| 2013/0317361 A1 | 11/2013 | Tabaru et al. |
| 2014/0081135 A1 | 3/2014 | Choi et al. |
| 2015/0005633 A1 | 1/2015 | Kanayama et al. |
| 2015/0141821 A1 | 5/2015 | Yoshikawa et al. |
| 2016/0345938 A1 | 12/2016 | Tanter et al. |
| 2017/0181729 A1 | 1/2017 | Tanter et al. |

FOREIGN PATENT DOCUMENTS

| | | |
|---|---|---|
| WO | 2011/064688 A1 | 6/2011 |
| WO | 2013/153968 A1 | 10/2013 |
| WO | 2014/162966 A1 | 10/2014 |

OTHER PUBLICATIONS

Debernard et al., "Characterization of muscle architecture in children and adults using magnetic resonance elastography and ultrasound techniques", Journal of Biomechanics, 2011, pp. 397-401, vol. 44.

* cited by examiner

United States Patent US 11,672,509 B2

SHEAR WAVE ELASTOGRAPHY METHOD AND APPARATUS FOR IMAGING AN ANISOTROPIC MEDIUM

CROSS-REFERENCE TO RELATED APPLICATION

This application is a continuation of U.S. patent application Ser. No. 15/539,170 filed on Jun. 23, 2017, which is the national phase of PCT International Application No. PCT/IB2014/003123 filed on Dec. 24, 2014, the contents of which are hereby incorporated by reference.

FIELD OF THE INVENTION

The present invention relates to imaging methods and apparatuses using shear waves, more precisely to shear wave elastography method and apparatuses for imaging anisotropic media.

BACKGROUND OF THE INVENTION

U.S. Pat. No. 7,252,004 describes an example of a shear wave elastography method for imaging a viscoelastic medium. While the method of U.S. Pat. No. 7,252,004 gives full satisfaction when the viscoelastic medium is homogeneous, the reproducibility and reliability of images and measurements is not optimal when the viscoelastic medium is an anisotropic medium containing fibers.

In fact, measurements and images obtained with shear wave elastography are computed from the observed displacement and/or deformation of the viscoelastic medium submitted to a shear wave.

Unfortunately, shear wave propagates differently in anisotropic medium containing fibers compared to homogeneous medium since their propagation parameters depend not only of the physical characteristics of the medium but also of the relative angle of the shear wave front with fibers directions.

Thus, depending on the relative angle of the shear wave propagation direction with fibers directions, the measured value of the propagation parameters of the shear wave can vary and gives non reliable and non reproducible measurements and images to the shear wave elastography.

The instant invention has notably for object to improve the situation.

SUMMARY OF THE INVENTION

To this aim, according to the invention, such a shear wave elastography method for imaging an anisotropic medium comprises a) an initial ultrasonic acquisition step during which at least one initial physical parameter is acquired in at least one region of interest in the anisotropic medium;

b) a spatial characterization step during which a set of spatial characteristics of the anisotropic medium is determined on the basis of the initial physical parameter; and c) a shear wave imaging step comprising:

c1) an excitation substep during which a shear wave is generated inside the anisotropic medium on the basis of said set of spatial characteristics; and c2) an observation substep during which the propagation of said shear wave is observed simultaneously at a multitude of points in the observation field.

In some embodiments, one might also use one or more of the following features:

the set of spatial characteristics of the anisotropic medium comprises at least one of the following: a direction, spatial angle or spatial position of anisotropic features in the at least one region of interest, and a preferred excitation spatial direction in the at least one region of interest;

the initial physical parameter is an image of the at least one region of interest in the anisotropic medium acquired using B-mode ultrasonic imaging;

the initial ultrasonic acquisition step comprises a shear wave imaging step comprising:

an excitation substep during which an shear wave is generated inside the anisotropic medium with at least one shear wave direction, and an observation substep during which the propagation of said shear wave is observed simultaneously at a multitude of points in the at least one region of interest to acquire an initial physical parameter;

the initial ultrasonic acquisition step comprises a plurality of shear wave imaging steps associated with a plurality of shear wave directions and with a plurality of initial physical parameters acquired in at least one region of interest in the anisotropic medium, each shear wave imaging step of the plurality of shear wave imaging steps comprising an excitation substep during which a shear wave is generated inside the anisotropic medium with an associated shear wave direction of the plurality of shear wave directions, and an observation substep during which the propagation of said shear wave is observed simultaneously at a multitude of points in the at least one region of interest to acquire an associated initial physical parameter of the plurality of initial physical parameters;

said initial physical parameters are images of the region of interest in the anisotropic medium acquired using shear wave imaging;

said initial physical parameters are shear wave propagation parameters, acquired in the at least one region of interest, using shear wave imaging;

said shear wave propagation parameters are selected from shear wave speed, shear modulus $\mu$, Young's modulus E, shear elasticity $\mu 1$, shear viscosity $\mu 2$;

during the initial ultrasonic acquisition step, at least two initial physical parameters are acquired, respectively associated to at least two distinct regions of interest in the anisotropic medium, and, during the spatial characterization step, at least two sets of spatial characteristics are determined, respectively on the basis of the at least two initial physical parameters, and respectively associated to the at least two distinct regions of interest in the anisotropic medium, and, during the shear wave imaging step, during the excitation substep, at least two shear waves are generated inside the anisotropic medium, respectively on the basis of the at least two sets of spatial characteristics, and, during the observation substep, the propagation of said at least two shear waves is observed simultaneously at a multitude of points in the observation field;

the spatial characterization step comprises extracting a set of spatial characteristics by performing features detection on at least one image of the anisotropic medium acquired during the initial ultrasonic acquisition step;

the spatial characterization step comprises comparing shear wave propagation parameters of the plurality of shear wave propagation parameters acquired during the initial ultrasonic acquisition step to determine a preferred excitation spatial direction in the anisotropic medium;

the spatial characterization step comprises displaying an image of the anisotropic medium acquired during the initial ultrasonic acquisition step to a user using a display device connected to a central processing unit, said user indicating spatial characteristics of the anisotropic medium using an input device connected to said central processing unit;

said user indicates spatial characteristics of the anisotropic medium by moving, using said input device, a position of a virtual line displayed above said image of the anisotropic medium on said display device, said line being indicative of a spatial characteristic of the anisotropic medium;

said user indicates spatial characteristics by measuring, on said image of the anisotropic medium displayed on the display device, a numerical value of a spatial characteristic of the anisotropic medium using conventional angle measurement tools provided by an ultrasound system, said user then entering said numerical value in the central processing unit using the input device;

the shear wave is generated by emitting at least one focused ultrasound waves in the anisotropic medium using an array of transducers controlled by the central processing unit, the location of the focal points of said focused ultrasound waves and the timing of said focused ultrasound waves being determined by the central processing unit on the basis of the set of spatial characteristics of the anisotropic medium;

the location of the focal points and the timing of the plurality of focused ultrasound waves generating the shear wave are determined so that a wave front of said shear wave is substantially perpendicular to at least one of: a direction of anisotropic features in the anisotropic medium and a preferred excitation spatial direction in the anisotropic medium;

the location of the focal points and the timing of the plurality of focused ultrasound waves generating the shear wave are determined so that a propagation direction of said shear wave is substantially aligned with at least one of: a direction of anisotropic features in the anisotropic medium and a preferred excitation spatial direction in the anisotropic medium;

the observation substep comprises the operations of:

c2-1) causing an array of transducers that are controlled independently of one another to emit into the anisotropic medium a succession of ultrasound waves with spatial coverage and timing adapted so that said ultrasound waves exhibit at least partial spatial and temporal overlap with the propagating shear wave in the observation field, and c2-2) causing sound signals received from the anisotropic medium to be detected and recorded in real time by said array of transducers, said signals comprising echoes generated by the ultrasound waves interacting with scatterers in said anisotropic medium, the shear wave imaging step c) further comprising at least one processing substep c3) during which:

c3-1) the sound signals received successively from the anisotropic medium during operation c2-2) are processed in order to determine successive propagation images of the shear wave, and c3-2) at least one movement parameter of the anisotropic medium is determined at different points of the observation field;

during the initial ultrasonic acquisition step, a shear wave propagating along at least two shear wave directions is generated inside the anisotropic medium, and during the processing substep, sound signals received from the anisotropic medium are filtered according to the at least two shear wave directions to determine said at least one initial physical parameter;

said movement parameter is a displacement of the anisotropic medium;

at said operation c2-1), said unfocused ultrasound compression waves are emitted at a rate of at least 300 shots per second;

the focused ultrasound wave emitted during excitation substep presents a frequency f lying in the range 0.1 MHz to 100 MHz, and is emitted for a duration of k/f seconds, where k is an integer lying in the range 50 to 5000 and f is expressed in Hz;

the focused ultrasound wave emitted during excitation substep presents a frequency lying in the range 0.5 MHz to 15 MHz and is emitted during a succession of emission periods separated by rest periods, the emission periods following one another at a rate lying in the range 10 to 1000 emissions per second;

the focused ultrasound wave emitted during excitation substep c1) is a linear combination of two monochromatic signals having respective frequencies f1 and f2 such that $20 \text{ Hz} \leq |f1-f2| \leq 1000 \text{ Hz}$;

a focused ultrasound wave emitted during excitation substep is focused simultaneously on a plurality of focal points;

image processing substep is followed by a mapping substep during which, on the basis of variation in the movement parameter over time, at least one shear wave propagation parameter is calculated at at least some points of the observation field in order to determine a map of said propagation parameter in the observation field;

the shear wave propagation parameter which is calculated during mapping substep is selected from shear wave speed, shear modulus, Young's modulus, shear wave attenuation, shear elasticity, shear viscosity, mechanical relaxation time and the inverse of local strain;

substeps are repeated successively while emitting different plurality of focused ultrasound waves during successive excitation substeps, and then combining the maps obtained during the successive mapping substeps in order to calculate a combination map of the observation field;

steps b) and c) are reiterated at least once, a map of a propagation parameter in the observation field acquired during step c) at iteration n being used as initial physical parameter for step b) at iteration n+1.

The invention also has as an object, an imaging apparatus for implementing a shear wave elastography method as detailed above for imaging an observation field in an anisotropic medium, the apparatus comprising an array of transducers that are controlled independently of one another by at least one electronic central unit adapted:

to acquire at least one initial physical parameter in at least one region of interest in the anisotropic medium;

to determine a set of spatial characteristics of the anisotropic medium on the basis of the initial physical parameter;

to cause an shear wave to be generated inside the anisotropic medium on the basis of said set of spatial characteristics; and to observe the propagation of said shear wave simultaneously at a multitude of points in the observation field.

With these features, the shear wave characteristics and in particular the wave front and the propagation direction of the shear wave can be determined on the basis of the spatial characteristics of the anisotropic medium. This strongly improves the quality, reliability and reproducibility of the images and measurement obtained by shear wave elastography and imaging.

BRIEF DESCRIPTION OF THE DRAWINGS

Other features and advantages of the invention appear from the following detailed description of one embodiment thereof, given by way of non-limiting example, and with reference to the accompanying drawings.

In the drawings.

DETAILED DESCRIPTION

Figure 1:
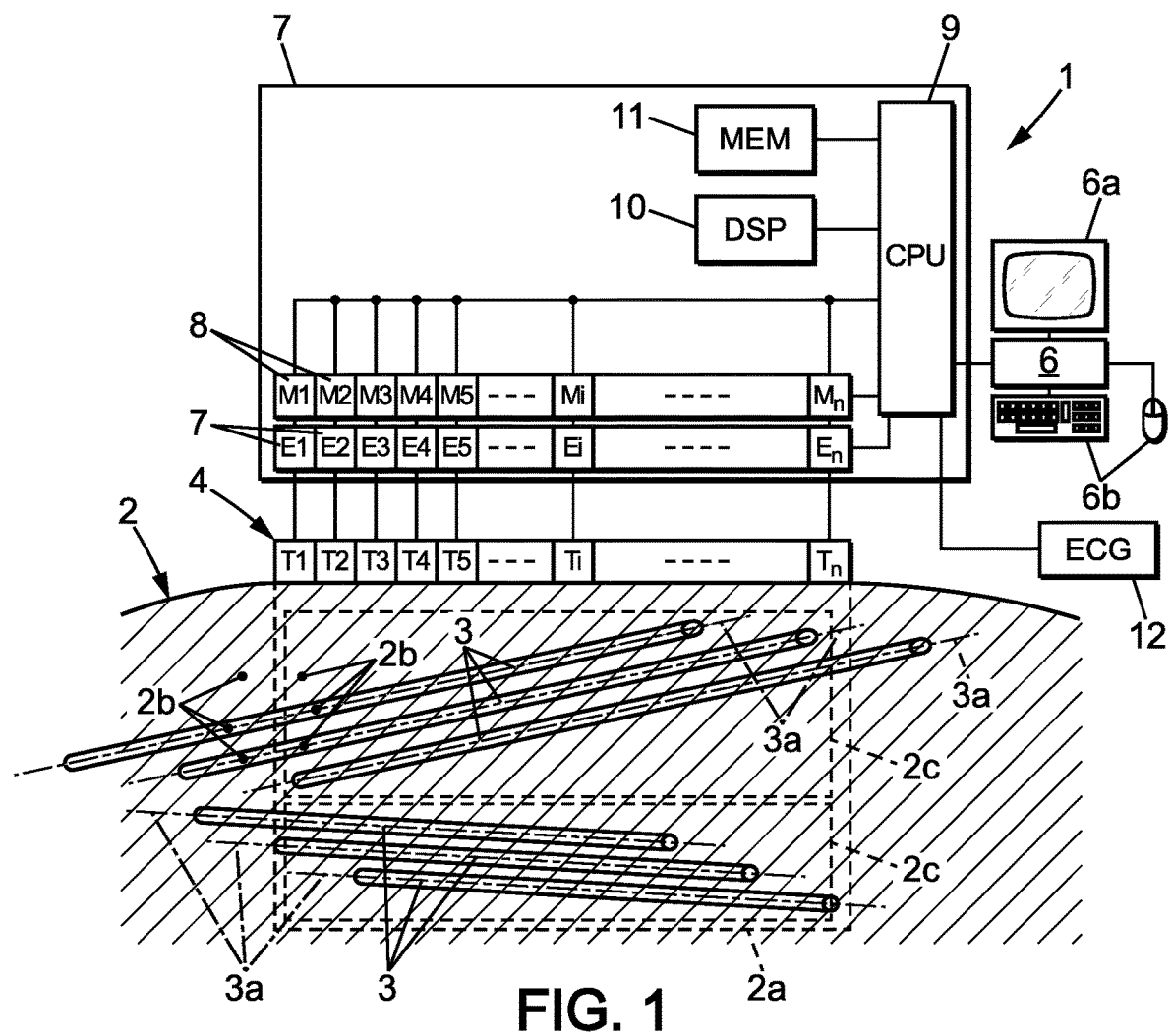
FIG. 1 is a diagrammatic view of a shear-wave imaging device in an embodiment of the invention.

The apparatus 1 shown on FIG. 1 is adapted for imaging an observation field 2a in an anisotropic medium 2.

The anisotropic medium 2 contains anisotropic features 3 which present identifiable spatial extension directions 3a. Anisotropic features 3 can be for instance fibers, tissue interfaces or anisotropic tissues, vessels, nerves, anisotropic constituents such as elongated cells or organelles and more generally any spatially oriented constituent of a tissue, in particular a living tissue.

Anisotropic medium 2 can for instance be a part of a living patient containing muscles or tendons. Such tissues contain anisotropic features 3 in the form of fibers 3, for instance muscles fascicles surrounded by perimysium, or arrays of collagen fibers in tendons, ligaments and fasciae. Such fibers 3 are strongly anisotropic and present identifiable spatial extension directions 3a, thus rendering the medium 2 anisotropic. Some fibers 3 might also be grouped in bundles of fibers usually extending along parallel directions 3a.

More precisely, the apparatus 1 is used to perform shear wave elastography of the anisotropic medium 2 to obtain an image or a measurement of shear wave propagation parameters in the observation field 2a.

A conventional shear wave elastography measurement or imaging is carried out by:
 having a mechanical shear wave 14 propagates through the anisotropic medium 2, in particular through the observation field 2a; and
 observing the propagation of this shear wave 14 in the observation field 2a through reflexion of ultrasonic waves on scatterers 2b which are reflective for the ultrasound waves and are naturally contained in biological tissues.

The particles 2b may be constituted by any non-uniformity in the anisotropic medium 2, for instance particles of collagen or more generally any inhomogeneity having a density that differs for the density of the surrounding medium.

Shear wave elastography measurements and images are then processed based on the observed displacement and/or deformation of tissues when penetrated by the shear wave.

As already mentioned, shear wave propagates differently in anisotropic media compared to homogeneous media.

In particular, the propagation of the shear wave depends not only on the physical characteristics of the medium 2 but also on the angle of the shear wave front, or of the shear wave propagation direction 14a, with favored directions 3a in the anisotropic medium 2.

Consequently, depending for instance on the relative angle of the shear wave propagation direction 14a with anisotropic features 3, the measured value of the propagation parameters of the shear wave 14 can vary thus giving non reliable and non reproducible shear wave elastography measurements and images.

The structure and general way of operation of a shear wave imaging step c) such as the one performed by apparatus 1 has already been described in details in document U.S. Pat. No. 7,252,004 and will be shortly recalled hereafter.

The apparatus 1 may include for instance:
 an ultrasound transducer array 4, for instance a linear array typically including n ultrasonic transducers $T_1$-$T_n$ juxtaposed along an axis as already known in usual echographic probes (the array 4 is then adapted to perform a bidimensional (2D) imaging of the observation field, but the array 4 could also be a bidimensional array adapted to perform a 3D imaging of the observation field); the number n of transducers is more than 1, for instance a few tens (e. g. 100 to 300); the transducers $T_1$-$T_n$ deliver ultrasound wave pulses, which pulses are of the type commonly used in echography, for example having a frequency lying in the range 0.5 MHz to 100 MHz, and preferably in the range 0.5 MHz to 15 MHz, e.g. being about 2.5 MHz;
 an electronic bay 5 controlling the transducer array 4 and acquiring signals there from;
 a microcomputer 6 for controlling the electronic bay 5 and viewing ultrasound images obtained from the electronic bay, said computer 6 including a display unit 6a, for instance a screen, and input devices 6b such as a keyboard, a mouse or other user interfaces.

The electronic bay 5 and the microcomputer 6 will be referred herein as the control system of the apparatus 1. Such control system might be constituted of more than two devices, or by one single electronic device could fulfill all the functionalities of the electronic bay 5 and of the microcomputer 6.

The electronic bay 5 may include for instance:
 n analog/digital converters 7 ($E_1$-$E_n$) individually connected to the n transducers ($T_1$-$T_n$) of the transducer array 4;
 n buffer memories 8 ($M_1$-$M_n$) respectively connected to the n analog/digital converters 7;
 a central processing unit 9 (CPU) communicating with the buffer memories 8 and the microcomputer 6;
 a digital signal processor 11 (DSP) connected to the central processing unit 9;
 a memory 10 (MEM) connected to the central processing unit 8.

The transducers $T_1$-$T_n$ are controlled independently of one another by the central processing unit 9. The transducers T1-Tn can thus emit selectively:
 an unfocussed ultrasound wave;
 or a focused ultrasound wave that is focused on one or more points of the observation field 2a.

The wording "unfocussed ultrasound wave" as understood herein means any unfocussed wave illuminating the entire observation field 2a, for instance:

an ultrasound compression wave that is "plane" (i.e. a wave whose wave front is rectilinear in the X,Y plane), or any other type of unfocused wave;

a wave generated by causing random sound signals to be emitted by the various transducers $T_1$-$T_n$;

a diverging wave, for instance a spherical waves;

a wave focused simultaneously on several focal points;

a weakly focusing waves (known as "fat" transmit focusing: ratio Focal distance/Aperture>2.5);

or more generally any kind of transmit waves that do not correspond to conventional focusing using a single focal point location and a ratio Focal distance/Aperture<2.5.

During operation of the apparatus 1, the transducer array 4 is placed in contact with the anisotropic medium 2, for instance with the skin of a patient.

The way of operation of the apparatus 1 is controlled by the control system, i.e. the central processing unit 9 and/or the computer 6, which are programmed for this way of operation. These two devices will hereafter be called the control system of apparatus 1 (of course, the control system could be different from the particular example described herein and in particular could be constituted by one single electronic device as recalled before, or by more than two electronic devices).

The operation of apparatus 1 to perform shear wave imaging will now be described in relation with shear wave imaging step c) but also apply to embodiments of the initial ultrasonic acquisition step a) in which initial physical parameters are acquired by shear wave imaging or elastography as described in further details hereafter.

The control system 6, 9 of the apparatus 1 is programmed to perform several substeps in succession, starting with an excitation substep c1) during which the control system 6, 9 causes a shear wave 14 to be generated in the observation field 2a by causing at least one focused ultrasound wave 13, focused on a focal point 13a of the anisotropic medium 2, to be emitted by the array 4 (this focussed wave 13 may be emitted by all or part of the transducers $T_1$-$T_n$);

In particular and as it will be further detailed below, the focused ultrasound waves 13 emitted during excitation substep c1) may be focused on a plurality of points 13a simultaneously or at different times so that the shear wave 14 as generated presents a desired wave shape.

It is thus possible to generate a shear wave 14 that is plane, or on the contrary a shear wave that is focused) and illuminates desired zones in the observation field 2a of the anisotropic medium 2.

In particular, the shear wave 14 can present a shear wave front and a shear wave direction 14a that can be controlled by the position of the focal points 13a and the timing of the emission of the focused ultrasound waves 13.

Figure 2A:
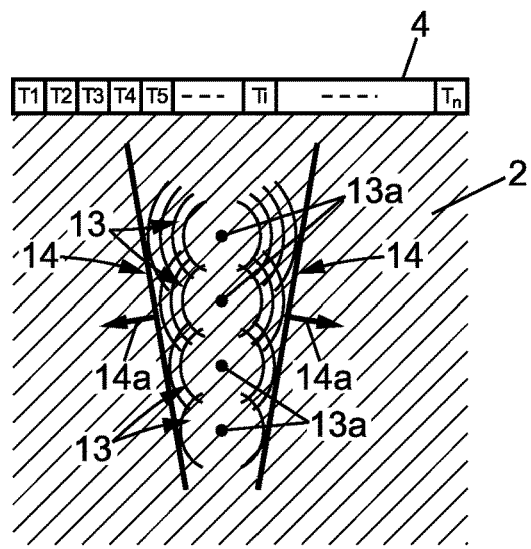
FIGS. 2a, 2b and 2c are schematic views of several shear waves generated in an anisotropic medium by different plurality of focused ultrasound waves.

With reference to FIG. 2a, a specific shear wave 14 can thus be generated by the emission of several focused ultrasound waves 13 simultaneously or within a short period of time, said ultrasound waves 13 having focal points 13a aligned along a line in the anisotropic medium 2.

The resulting shear wave 14 has a shear wave front that is substantially parallel to the alignment line of the focal points 13a and a propagation direction 14a that is substantially perpendicular to said line.

Figure 2B:
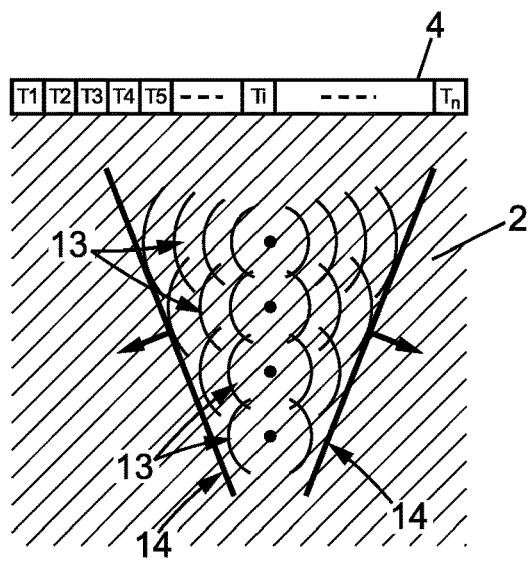

With reference to FIG. 2b, a specific shear wave 14 is illustrated that is generated by the emission of several focused ultrasound waves 13 with a longer period of time separating each emission, said ultrasound waves 13 having focal points 13a aligned along a line in the anisotropic medium 2.

The resulting shear wave 14 has a shear wave front with a higher angle relative to the alignment line of the focal points 13a than the above shear wave illustrated on FIG. 2a.

Figure 2C:
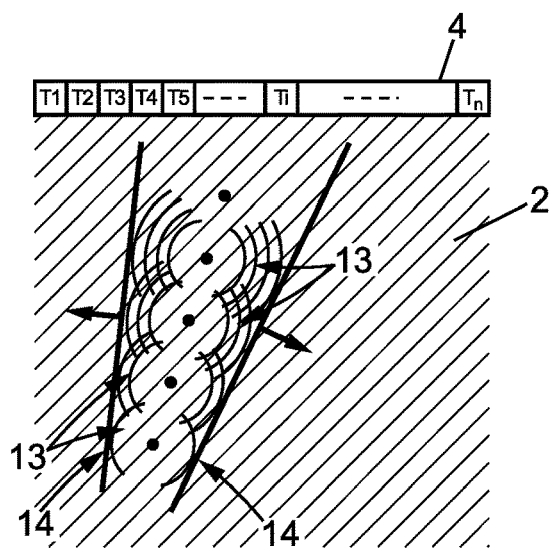

Referring now to FIG. 2c, another specific shear wave 14 is illustrated that is generated by the emission of several focused ultrasound waves 13 having focal points 13a aligned along a different line in the anisotropic medium 2, said line being inclined relatively to a vertical direction perpendicular to the array 4.

FIGS. 2a, 2b and 2c thus illustrates some of the various shear wave 14, that can be generated by the control system 6, 9 of the apparatus 1 by varying the position of the focal points 13a of the focused ultrasound waves 13 and the timing of the emission of the focused ultrasound waves 13.

Other types of shear wave 14 can also be generated, for instance, by varying the position of the focal points 13a of the focused ultrasound waves 13 and the timing of the emission of the focused ultrasound waves 13, the control system 6, 9 of the apparatus 1 may generate a shear wave 14 propagating along two or more shear wave directions. By "two shear wave directions", it is understood that said shear wave directions are not collinear.

The focused ultrasound wave emitted during the excitation substep c1) may be a monochromatic wave of frequency f lying in the range 0.5 MHz to 15 MHz, for example being equal to about 2.5 MHz, which is emitted for a duration of k/f seconds, where k is an integer lying in the range 50 to 5000 (e.g. being about 500) and f is expressed in Hz. Such a wave may possibly be emitted during a succession of emission periods separated by rest periods, the emission periods following one another at a rate lying in the range 5 to 1000 emissions per second.

In a variant, the focused ultrasound wave emitted during excitation substep c1) is a linear combination (in particular a sum) of two monochromatic signals of respective frequencies f1 and f2 such that 20 Hz≤|f1−f2|≤1000 Hz, thus producing an amplitude modulated wave having a modulation frequency |f1−f2|.

The apparatus 1 then performs an observation substep c2) during which the propagation of the shear wave 14 is observed simultaneously at a multitude of points of the observation field 2a), this observation step comprising the following operations:

c2-1) the control system 6, 9 causes the array 4 to emit into the anisotropic medium a succession of unfocused ultrasound compression waves (these unfocussed waves may be emitted by all or part of the transducers $T_1$-$T_n$) at a rate of at least 300 shots per second, for instance at least 500 shots/s (the focusing and the timing of the focussed ultrasound wave emitted in step a), and the timing of said unfocused ultrasound waves are adapted so that at least some of said unfocused ultrasound waves reach the observation field during the propagation of the shear wave through the observation field);

c2-2) the control system 6, 9 causes the array 4 to detect sound signals received from the anisotropic medium 2 (this detection can be carried out by all or part of the transducers of the array 4), said signals comprising echoes generated by the unfocused ultrasound compression wave interacting with scatterers 2b in the observation field, these echoes corresponding (directly or indirectly) to successive images of the displacement of the anisotropic medium 2; the detected signals are recorded in real time in the buffer memories $M_1$-$M_n$;

The apparatus 1 then performs at least one processing substep c3) during which:

c3-1) the control system 6, 9 processes the successive sound signals received from the anisotropic medium 2 during operation c2-2) in order to determine successive propagation images; and c3-2) the control system 6, 9 determines at least one movement parameter for the anisotropic medium 2 at various points in the observation field 2a.

It should be noted that the above operation c3-1) could be omitted: more generally, the method of the invention does not require determining propagation images, and the control system 6, 9 may determine said movement parameter by any other means.

During operation c2-1), which may last for example 0.1 to 180 s, it is possible to emit unfocused ultrasound compression waves at a rate lying in the range 500 to 10,000 shots per second, and preferably in the range 1000 to 5000 shots per second (with this rate being limited by the go-and-return travel time for the compression wave through the patient's body 2: it is necessary for all of the echoes that are generated by the compression wave to have been received by the probe 6 before a new compression wave is sent).

In the embodiment wherein the shear wave, emitted during the initial ultrasonic acquisition step, propagates along two or more shear wave directions, sound signals received from the anisotropic medium may be filtered, during the processing substep, according to said shear wave directions to determine said initial physical parameter.

In one embodiment, the sound signals received from the anisotropic medium are filtered to determine two or more initial physical parameters respectively associated to the two or more shear wave directions.

Such a filtering operation may for instance be a temporal or spatial filtering of the successive sound signals received from the anisotropic medium 2 during operation c2-2) or of the movement parameters determined during operation c3-2).

Each unfocused ultrasound compression wave propagates through the patient's body 2 at a propagation speed that is much higher than that of shear waves (e.g. about 1500 m/s in the human body), and interacts with the reflecting particles 2b, thereby generating echoes or other analogous disturbances in the signal that are known in themselves under the name "speckle noise" in the field of echography.

The speckle noise is picked up by the transducers $T_1$-$T_n$ during substep b2), after each shot of an unfocused ultrasound compression wave. The signal $s_{ij}(t)$ as picked up in this way by each transducer $T_i$ after shot No. j is initially sampled at high frequency (e.g. 30 MHz to 100 MHz) and digitized (e.g. on 12 bits) in real time by the analog/digital converter $E_i$ corresponding to transducer $T_i$.

The signal $s_{ij}(t)$ as sampled and digitized in this way is then stored, likewise in real time, in a the buffer memory $M_i$ corresponding to the transducer $T_i$.

By way of example, each memory Mi may present a capacity of about 128 megabytes (MB), and contains all of the signals $s_{ij}(t)$ received in succession for shots j=1 to p.

In deferred time, after all of the signals $s_{ij}(t)$ corresponding to the same propagation of a shear wave have been stored, the central unit 9 processes these signals (or have them processed by another circuit such a summing circuit, or the computer 6 may process the signals itself) using a conventional path-forming step corresponding to substep c1).

This generates signals $S_j(x,y)$ each corresponding to the image of the observation field after shot No. j.

For example, it is possible to determine a signal $S_j(t)$ by the following formula:

$$S_j(t) = \sum_{i=1}^{n} \alpha_i(x,y) \cdot s_{ij}[t(x,y) + d_i(x,y)/V]$$

where:

$s_{ij}$ is the raw signal perceived by the transducer No. i after ultrasound compression wave shot No. j;

t(x,y) is the time taken by the ultrasound compression wave to reach the point of the observation field having coordinates (x,y), with t=0 at the beginning of shot No. j;

$d_i(x,y)$ is the distance between the point of the observation field having coordinates (x,y) and transducer No. i, or an approximation to said distance;

V is the mean propagation speed of ultrasound compression waves in the viscoelastic medium under observation; and $\alpha_i(x,y)$ is a weighting coefficient taking account of apodization relationships (in practice, in numerous cases, it is possible to assume that $\alpha_i(x,y)=1$).

The above formula applies mutatis mutandis when the observation field is three-dimensional (with a two-dimensional array of transducers), with space coordinates (x,y) being replaced by (x,y,z).

After the optional path-forming step, the central unit 9 stores in the central memory M, the image signals $S_j(x,y)$ (or $S_j(x)$ if the image would be in 1 dimension only, or $S_j(x,y,z)$ in case of a 3D image), each corresponding to shot No. j. These signals may also be stored in the computer 6 if the computer itself performs the image processing.

These images are then processed in deferred time in operation c3-2) by correlation and advantageously by cross-correlation either in pairs, or preferably with a reference image, as explained in U.S. Pat. No. 7,252,004. The above-mentioned cross-correlation can be performed, for example, in the digital signal processor 11, or it may be programmed in the central unit 9 or in the computer 6.

During this cross-correlation process, a cross-correlation function $<S_j(x,y),S_{j+1}(x,y)>$ is maximized in order to determine the displacement to which each particle 2b giving rise to an ultrasound echo has been subjected.

Examples of such cross-correlation calculations are given in U.S. Pat. No. 7,252,004.

This produces a set of displacement vectors $\bar{u}(\bar{r},t)$ generated by the shear waves in each position $\bar{r}$ of the observation field 2a of the anisotropic medium 2 under the effect of the shear wave (these displacement vectors may optionally be reduced to a single component in the example described herein).

This set of displacement vectors is stored in the memory M or in the computer 6 and can be displayed, for example, in particular by means of the screen 4a of the computer, in the form of a slow motion picture in which the values of the displacements are illustrated by an optical parameter such as a gray level or a color level.

The propagation differences of the shear wave between zones having different characteristics in the anisotropic medium 2 can thus be seen clearly.

The motion picture of shear wave propagation can also be superposed on a conventional echographic image, which can also be generated by the apparatus 1 described above.

Furthermore, it is also possible to calculate, instead of displacements, the deformations of the anisotropic medium

2 for each of the points in the observation field 2*a*, i.e. vectors whose components are the derivatives of the displacement vectors respectively relative to the space variables (X and Y coordinates in the example described). These deformation vectors can be used like the displacement vectors for clearly viewing the propagation of the shear wave in the form of a motion picture, and they also present the advantage of eliminating displacements of the transducer array 4 relative to a patient's body under observation.

From the displacement or deformation fields, the computer 6 (or more generally the control system 6, 9) can advantageously then proceed with a map-making substep c4) during which, on the basis of the way in which the movement parameter (displacement or deformation) varies over time in the field of observation X, Y (or X, Y, Z with a two-dimensional array of transducers), it calculates at least one propagation parameter of the shear wave, either at certain points (at least 1 point) in the observation field 2*a* as selected by the user acting on the computer 6, or else throughout the observation field 2*a*.

The propagation parameter of the shear wave that is calculated during the map-making substep c4) is selected, for example, from amongst: the shear modulus μ, or Young's modulus E=3μ, or the propagation speed $c_s$ of shear waves $$(c_s = \sqrt{\frac{E}{3\rho}},$$

where ρ is the density of the tissues), or the shear elasticity μ1, as explained in more details in U.S. Pat. No. 7,252,004, or the inverse of local strain. Such propagation parameter is representative of the elasticity of the anisotropic medium constituting the observation field 2*a*.

This propagation parameter may be computed for instance by the computer 6, repeatedly at several different instants, several times per second (e.g. at a rate of at least 5 times per second, e.g. at least 10 times per second).

Preliminary to the shear wave imaging step c), the apparatus 1 performs several steps that will now be detailed further.

During an initial imaging step a), at least one initial physical parameter is acquired for at least one region of interest 2*c* in the anisotropic medium 2.

In a first embodiment, the initial physical parameter is acquired using B-mode ultrasonic imaging. The initial physical parameter can be, in particular, an image of the region of interest 2*c* in the anisotropic medium 2.

To this aim, the control system 6, 9 can perform a conventional B-mode ultrasound image of the observation field 2*a* using the transducer array 4 in a standard ultrasound way. Standard ultrasound imaging consists of an insonification of the medium with a cylindrical wave that focuses on a given point. Using the backscattered echoes of this single insonification, a complete line of the image is computed using a dynamic receive beamforming process.

In a second embodiment of the invention, the initial physical parameter is acquired using shear wave elastography or imaging.

In this second embodiment, the initial physical parameter can be a shear wave propagation parameter or an image obtained by shear wave imaging.

The control system 6, 9 may in particular acquire the image by performing a shear wave elastography or imaging similar to the shear wave imaging step c) described herebefore.

Thus, the initial ultrasonic acquisition step may comprises a shear wave imaging step comprising:

a1) an excitation substep during which a shear wave is generated inside the anisotropic medium with a shear wave direction; and a2) an observation substep during which the propagation of said shear wave is observed simultaneously at a multitude of points in the at least one region of interest to acquire an initial physical parameter.

Advantageously, the initial imaging step a), can comprise the acquisition of several initial physical parameters, each comprising step a1) and step a2).

Thus several shear wave propagation parameters may be measured at one or several points of interest 2*b* or within the region of interest 2*c* of the anisotropic medium.

Several images of the region of interest of the anisotropic medium may also be acquired.

The shear wave propagation parameters may for instance be selected from shear wave speed, shear modulus μ, Young's modulus E, shear elasticity μ1, shear viscosity μ2.

Then, in a spatial characterization step b), a set of spatial characteristics of the region of interest in the anisotropic medium is determined based on the initial physical parameter or the plurality of initial physical parameters.

The set of spatial characteristics may for instance comprises the direction of anisotropic features 3 or the spatial angle of the anisotropic features 3 with a reference plane or line such as the direction of extension of the transducer array 4, for instance the spatial angle of fibers direction 3*a* with the direction of extension of the transducer array 4. The set of spatial characteristics may also comprises the spatial position or location of the anisotropic features 3 in the anisotropic medium 2, in particular, the spatial position of said anisotropic features in the bidimensional (2D) or tridimensional (3D) imaging of the region of interest. The set of spatial characteristics may also comprise a preferred excitation spatial direction in the region of interest.

Advantageously, in a first embodiment of the invention, the initial physical parameters are B-mode or shear wave images and the spatial characterization step b) can be performed automatically. In particular, step b) may thus comprise the extraction of a set of spatial characteristics by performing features detection on at least one image of the observation field in the anisotropic medium acquired during the initial ultrasonic acquisition step.

In a variant of this first embodiment of the invention, the spatial characterization step b) may be performed manually.

To this aim, a B-mode or shear wave image may be displayed on the display device 6*a* to be seen by a user, for instance a medical practitioner or an operator using apparatus 1.

Said user can then indicate spatial characteristics of fibers 3 using the input devices 6*b* connected to said central processing unit 6, 9.

In a first variant of the invention, user indicates spatial characteristics of fibers 3 by moving the position of a virtual line displayed above the image of the anisotropic medium on said display device, said line being indicative of a direction of fibers. The user can for instance move said line using the input devices 6*b*, for instance the mouse and the keyboard.

In another variant, the user measures a numerical value of a spatial angle of fibers on the image of the anisotropic medium displayed on the display device. The user can perform this measurement using for instance conventional angle measurement tools provided on every standard ultrasound system.

The user can then enter the measured numerical value in the central processing unit using the input device in order to indicate spatial characteristics of fibers 3.

In a third embodiment, of the invention, the initial physical parameters are shear wave propagation parameters and the spatial characterization step b) may also be performed automatically as follow.

In this embodiment, the initial ultrasonic acquisition step a) may advantageously comprise a plurality of shear wave imaging steps associated with a plurality of shear wave directions and with a plurality of initial physical parameter acquired in at least one region of interest in the observation field in the anisotropic medium.

More precisely, each shear wave imaging step is performed substantially as described here before in relation with shear wave imaging step c). Thus, each shear wave imaging step comprises first an excitation substep a1) during which a shear wave is generated inside the anisotropic medium with an associated shear wave direction of the plurality of shear wave directions. Thus several shear waves are generated having distinct shear wave directions.

Each shear wave imaging step further comprises an observation substep a2) during which the propagation of the shear wave is observed simultaneously at a multitude of points in the observation field to acquire an associated initial physical parameter, being advantageously a shear wave propagation parameter in this embodiment.

Following this initial ultrasonic acquisition step a), the spatial characterization step b) then comprises a comparison of the acquired shear wave propagation parameters together in order to determine a preferred excitation spatial direction in the anisotropic medium.

For instance, when the acquired shear wave propagation parameters are shear wave speeds, the highest value of the acquired shear wave speed among the plurality acquired shear wave speeds may advantageously be correlated with an excitation shear wave direction having the best alignment with the anisotropic features 3 among the plurality of excitation shear wave directions employed during the initial ultrasonic acquisition step a). It is thus possible to determine a preferred excitation spatial direction in the anisotropic medium 2.

Step a) and b) may also be performed for two or more points of interests and two or more regions of interest. This may be advantageous for instance when the observation field of the anisotropic medium presents several regions having distinct spatial properties. For instance, a first region of the observation field may contain fibers oriented along a first direction while a second region of the observation field may contain vessels oriented along a second direction.

In this case, it is thus advantageous to define a first and a second distinct region of interest, respectively comprised within the first and the second region of the observation field.

The set of spatial characteristics of the anisotropic medium determined during step b) may then comprises a first set of spatial characteristics associated with the first region of interest and a second set of spatial characteristics associated with the second region of interest.

More than two regions of interest may be defined depending on the anisotropic medium 2.

When the set of spatial characteristics has been determined, the control system 6, 9 of the apparatus 1 can then generate a shear wave 14 adapted to the spatial characteristics of the anisotropic medium 2 by varying the position of the focal points 13a of the focused ultrasound waves 13 and the timing of the emission of the focused ultrasound waves 13 as detailed here-above in relation with substep c1).

In particular, the control system 6, 9 of the apparatus 1 can then generate an shear wave whose propagation direction is substantially aligned with the spatial extension directions 3a of the anisotropic features 3.

The control system 6, 9 of the apparatus 1 can also generate an shear wave whose shear wave front is substantially perpendicular to the spatial extension directions 3a of the anisotropic features 3.

When more than two regions of interest are defined, the spatial characteristics of the shear wave, in particular the shear wave propagation directions, may then be adapted for each regions of interest. Thus, a shear wave having at least two propagation directions may be generated. Such a shear wave is for instance a spherical wave and in particular may thus be a wave that is not a plane wave but a complex wave.

Alternatively, several shear waves may be emitted each being generated on the basis of spatial characteristics associated with a region of interest.

The spatial characterization step b) and the shear wave imaging step c) may also be reiterated to further refine the set of spatial characteristics.

An image obtained during step c) of iteration n, for instance a map of a propagation parameter determined by a map-making substep c4), can then be used as the initial physical parameter for step b) at iteration n+1.

It should be noted that the method of the invention may further include a tracking step or substep for tracking deformations and displacement of the anisotropic medium 2 (in particular of anisotropic features 3) so that the measurements of ultrasonic parameter are done at a same location within the anisotropic medium 2.

Besides, shear wave imaging as described above may be coupled with conventional ultrasound imaging provided in real time by the same apparatus.

The invention claimed is:

1. A shear wave elastography method for imaging an observation field in an anisotropic medium, the method comprising:
   a) an initial ultrasonic acquisition step of acquiring at least one initial physical parameter in at least one region of interest in the anisotropic medium;
   b) a spatial characterization step of determining a set of spatial characteristics of the anisotropic medium based on the initial physical parameter, said set of spatial characteristics comprising a direction or a spatial angle of an anisotropic feature in the at least one region of interest; and
   c) a shear wave imaging step comprising:
      c1) an excitation substep of generating the shear wave inside the anisotropic medium based on said set of spatial characteristics, the shear wave being generated by emitting at least one focused ultrasound wave in the anisotropic medium using an array of transducers controlled by a central processor, the location of focal points of said at least one focused ultrasound wave and the timing of said at least one focused ultrasound wave being determined by the central processor based on the extracted set of spatial characteristics of the anisotropic medium, the location of the focal points and the timing of the plurality of focused ultrasound waves generating the shear wave being determined so that a wave front of said shear wave is perpendicular to at least one of: a direction of detected anisotropic features in the anisotropic medium, and a selected excitation spatial direction in the anisotropic medium, c2) an observation substep of observing the propagation of said shear wave simultaneously at a multitude of points in the observation field.

2. The method according to claim 1, wherein the set of spatial characteristics of the anisotropic medium further comprises at least one of the following: a direction, spatial angle or spatial position of anisotropic features in the at least one region of interest, and a specific excitation spatial direction in the at least one region of interest.

3. The method according to claim 1, wherein the initial physical parameter is an image of the at least one region of interest in the anisotropic medium acquired using B-mode ultrasonic imaging.

4. The method according to claim 1, wherein the initial ultrasonic acquisition step comprises an initial shear wave imaging step comprising:
- a1) an excitation substep of generating an initial shear wave is generated inside the anisotropic medium with at least one shear wave direction, and
- a2) an observation substep of observing the initial shear wave simultaneously at a multitude of points in the at least one region of interest to acquire an initial physical parameter.

5. The method according to claim 4, wherein
the initial ultrasonic acquisition step comprises a plurality of shear wave imaging steps associated with a plurality of shear wave directions and with a plurality of initial physical parameters acquired in at least one region of interest in the anisotropic medium,
each shear wave imaging step of the plurality of shear wave imaging steps comprising:
- a1) an excitation substep of generating inside the anisotropic medium with an associated shear wave direction of the plurality of shear wave directions; and
- a2) an observation substep of observing the propagation of said respective shear wave simultaneously at a multitude of points in the at least one region of interest to acquire an associated initial physical parameter of the plurality of initial physical parameters.

6. The method according to claim 4, wherein said at least one initial physical parameter is image data of the region of interest in the anisotropic medium acquired using shear wave imaging.

7. The method according to claim 4, wherein said at least one initial physical parameter is at least one shear wave propagation parameter, acquired in the at least one region of interest, using shear wave imaging.

8. The method according to claim 7, wherein said at least one shear wave propagation parameter is selected from shear wave speed, shear modulus $\mu$, Young's modulus E, shear elasticity $\mu 1$, shear viscosity $\mu 2$.

9. The method according to claim 1,
wherein during the initial ultrasonic acquisition step a), at least two initial physical parameters are acquired, respectively associated to at least two distinct regions of interest in the anisotropic medium;
wherein during the spatial characterization step b), at least two sets of spatial characteristics are determined, respectively based on the at least two initial physical parameters, and respectively associated to the at least two distinct regions of interest in the anisotropic medium, and
wherein during the shear wave imaging step c),
during the excitation substep c1), at least two shear waves are generated inside the anisotropic medium, respectively based on the at least two sets of spatial characteristics, and
during the observation substep c2), the propagation of said at least two shear waves is observed simultaneously at a multitude of points in the observation field.

10. The method according to claim 1, wherein the spatial characterization step b) comprises extracting the set of spatial characteristics by performing features detection on at least one image of the anisotropic medium acquired during the initial ultrasonic acquisition step a).

11. The method according to claim 1, wherein the spatial characterization step b) comprises comparing shear wave propagation parameters of the plurality of shear wave propagation parameters acquired during the initial ultrasonic acquisition step a) to determine a preferred excitation spatial direction in the anisotropic medium.

12. The method according to claim 1, wherein the spatial characterization step b) comprises displaying an image of the anisotropic medium acquired during the initial ultrasonic acquisition step a) to a user using a display device connected to a central processing unit, said user indicating spatial characteristics of the anisotropic medium using an input device connected to said central processing unit.

13. The method according to claim 12, wherein said user indicates the spatial characteristics of the anisotropic medium by moving, using said input device, a position of a virtual line displayed above said image of the anisotropic medium on said display device, said line being indicative of a spatial characteristic of the spatial characteristics of the anisotropic medium.

14. The method according to claim 12, wherein said user indicates the spatial characteristics by measuring, on said image of the anisotropic medium displayed on the display device, a numerical value of a spatial characteristic of the anisotropic medium using conventional angle measurement tools provided by an ultrasound system, said user then entering said numerical value in the central processing unit using the input device.

15. The method according to claim 1, wherein the location of the focal points and the timing of the plurality of focused ultrasound waves generating the shear wave are determined so that a propagation direction of said shear wave is aligned with at least one of:
- a direction of anisotropic detected features in the anisotropic medium, and
- a selected excitation spatial direction in the anisotropic medium.

16. The method according to claim 1, wherein the observation substep c2) comprises the operations of:
- c2-1) causing an array of transducers that are controlled independently of one another to emit into the anisotropic medium a succession of ultrasound waves with spatial coverage and timing configured so that said ultrasound waves exhibit at least partial spatial and temporal overlap with the propagating shear wave in the observation field, and
- c2-2) causing sound signals received from the anisotropic medium to be detected and recorded in real time by said array of transducers, said signals comprising echoes generated by the ultrasound waves interacting with scatterers in said anisotropic medium, the shear wave imaging step c) further comprising at least one processing substep c3) during which:
- c3-1) the sound signals received successively from the anisotropic medium during operation c2-2) are processed in order to determine successive propagation images of the shear wave, and c3-2) at least one movement parameter of the anisotropic medium is determined at different points of the observation field.

17. The method according to claim 16, wherein, during the initial ultrasonic acquisition step, an initial shear wave propagating along at least two shear wave directions is generated inside the anisotropic medium, and during the processing substep, sound signals received from the anisotropic medium are filtered according to the at least two shear wave directions to determine said at least one initial physical parameter.

18. The method according to claim 16, wherein said movement parameter is a displacement of the anisotropic medium.

19. The method according to claim 16, wherein at said operation c2-1), said unfocused ultrasound compression waves are emitted at a rate of at least 300 shots per second.

20. The method according to claim 16, wherein the focused ultrasound wave emitted during excitation substep c1) presents a frequency f lying in the range 0.1 MHz to 100 MHz, and is emitted for a duration of k/f seconds, where k is an integer lying in the range 50 to 5000 and f is expressed in Hz.

21. The method according to claim 16, wherein the focused ultrasound wave emitted during excitation substep c1) presents a frequency lying in the range 0.5 MHz to 15 MHz and is emitted during a succession of emission periods separated by rest periods, the emission periods following one another at a rate lying in the range 10 to 1000 emissions per second.

22. The method according to claim 16, wherein the focused ultrasound wave emitted during excitation substep c1) is a linear combination of two monochromatic signals having respective frequencies f1 and f2 such that $20\ Hz \leq |f1-f2| \leq 1000\ Hz$.

23. The method according to claim 16, wherein a focused ultrasound wave emitted during excitation substep c1) is focused simultaneously on a plurality of focal points.

24. The method according to claim 16, wherein the image processing substep c3) is followed by a mapping substep c4) during which, based on a variation in the movement parameter over time, at least one shear wave propagation parameter is calculated at at least some points of the observation field in order to determine a map of said propagation parameter in the observation field.

25. The method according to claim 24, wherein the shear wave propagation parameter which is calculated during the mapping substep c4) is selected from shear wave speed, shear modulus, Young's modulus, shear wave attenuation, shear elasticity, shear viscosity, mechanical relaxation time, and the inverse of local strain.

26. The method according to claim 24, wherein the substeps c1) to c4) are repeated successively while emitting different pluralities of focused ultrasound waves during successive excitation substeps c1), and then combining the maps obtained during the successive mapping substeps c4) in order to calculate a combination map of the observation field.

27. The method according to claim 24, wherein the steps b) and c) are reiterated at least once, a map of a propagation parameter in the observation field acquired during step c) at iteration n being used as the initial physical parameter for step b) at iteration n+1.

28. An imaging apparatus for imaging an observation field in an anisotropic medium, the apparatus comprising:

an array of transducers; and at least one electronic central processor controlling the transducers independently of one another, the at least one electronic central processor being configured to:

acquire the at least one initial physical parameter in at least one region of interest in the anisotropic medium, determine a set of spatial characteristics of the anisotropic medium based on the initial physical parameter, said set of spatial characteristics comprising a direction or a spatial angle of an anisotropic feature in the at least one region of interest, cause the shear wave to be generated inside the anisotropic medium based on said set of spatial characteristics, the shear wave being generated by emitting at least one focused ultrasound wave in the anisotropic medium using an array of transducers controlled by a central processor, the location of focal points of said at least one focused ultrasound wave and the timing of said at least one focused ultrasound wave being determined by the central processor based on the extracted set of spatial characteristics of the anisotropic medium, the location of the focal points and the timing of the plurality of focused ultrasound waves generating the shear wave being determined so that a wave front of said shear wave is perpendicular to at least one of:

a direction of detected anisotropic features in the anisotropic medium, and a selected excitation spatial direction in the anisotropic medium, and observe the propagation of said shear wave simultaneously at a multitude of points in the observation field.

* * * * *